United States Patent
Vanderberg et al.

(10) Patent No.: US 6,599,715 B1
(45) Date of Patent: Jul. 29, 2003

(54) REAL TIME VIABILITY DETECTION OF BACTERIAL SPORES

(75) Inventors: Laura A. Vanderberg, Los Alamos, NM (US); Timothy J. Herdendorf, Sullivan, WI (US); Richard J. Obiso, Gaithersburg, MD (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/570,137

(22) Filed: May 12, 2000

Related U.S. Application Data

(60) Provisional application No. 60/133,823, filed on May 12, 1999.

(51) Int. Cl.$^7$ .................................................. C12Q 1/04
(52) U.S. Cl. ........................................ 435/34; 435/242
(58) Field of Search ................................... 435/34, 242

(56) References Cited

U.S. PATENT DOCUMENTS

| | | | |
|---|---|---|---|
| 3,687,815 A | * 8/1972 | Scharpf | |
| 5,536,645 A | * 7/1996 | Jay | 435/32 |
| 5,795,730 A | 8/1998 | Tautvydas | 435/31 |
| 5,800,821 A | * 9/1998 | Acheson et al. | |
| 5,876,960 A | * 3/1999 | Rosen | |

OTHER PUBLICATIONS

CAPLUS abstract (Acc No. 1960:98190). Demain et al. (1960). Dissociation of spore germination from outgrowth by use of auxotrophic mutants of Bacillus subtilis. J. Bacteriol. 79: 783–788.*

Obiso et al, "Characterization of Bacillus Globigii Endospore Germination: A Real–Time Method of Detecting Endospore Viability," equivalent to Abstracts of the General Meeting of the American Society for Microbiology, May 1998, vol. 98, p. 308.

Thacker et al., "A Method for the Rapid Detection and Enumeration of Viable Bacteria," American Laboratory, pp. 20–23 (May 1998).

Rosen, "Bacterial Spore Detection and Determination by Use of Terbium Dipicolinate Photoluminescence," Analytical Chemistry, vol. 69, No. 6, pp. 1082–1085 (Mar. 15, 1997).

Sacks, "Chemical Germination of Native and Cation–Exchanged Bacterial Spores with Trifluoperazine," Applied and Environmental Microbiology, vol. 56, No. 4, pp. 1185–1187 (Apr. 1990).

Lamture et al., "Intensely Luminescent Immunoreactive Conjugates of Proteins and Dipicolinate–Based Polymeric Tb(III) Chelates," Bioconjugate Chem. No. 6, pp. 88–92 (1995).

* cited by examiner

Primary Examiner—Ralph Gitomer
(74) Attorney, Agent, or Firm—Bruce H. Cottrell

(57) ABSTRACT

This invention relates to a process for detecting the presence of viable bacterial spores in a sample and to a spore detection system, the process including placing a sample in a germination medium for a period of time sufficient for commitment of any present viable bacterial spores to occur, mixing the sample with a solution of a lanthanide capable of forming a fluorescent complex with dipicolinic acid, and, measuring the sample for the presence of dipicolinic acid, and the system including a germination chamber having inlets from a sample chamber, a germinant chamber and a bleach chamber, the germination chamber further including an outlet through a filtering means, the outlet connected to a detection chamber, the detection chamber having an inlet from a fluorescence promoting metal chamber and the detection chamber including a spectral excitation source and a means of measuring emission spectra from a sample, the detection chamber further connected to a waste chamber. A germination reaction mixture useful for promoting commitment of any viable bacterial spores in a sample including a combination of L-alanine, L-asparagine and D-glucose is also described.

7 Claims, 2 Drawing Sheets

REAL TIME VIABILITY DETECTION OF BACTERIAL SPORES

Figure 1:
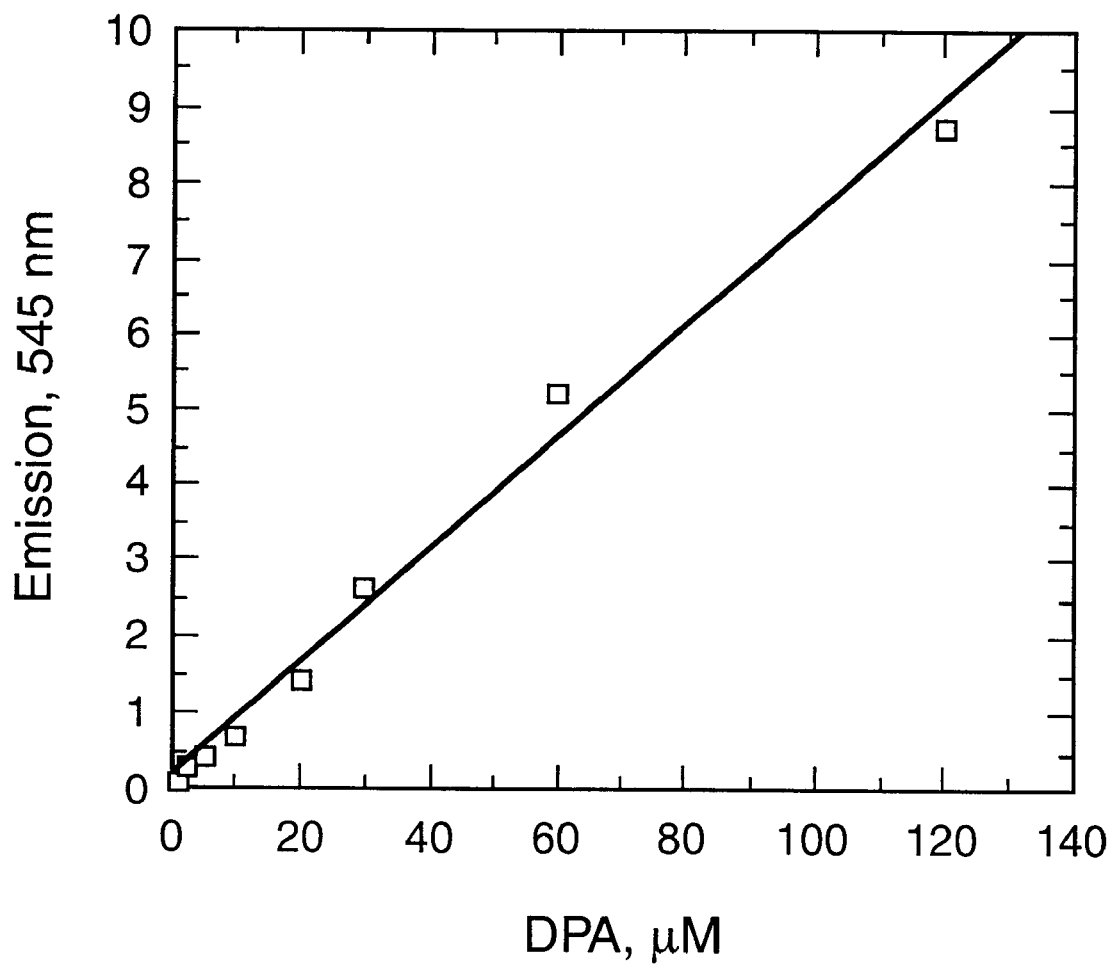

This application claims the benefit of U.S. provisional application Ser. No. 60/133,823, filed May 12, 1999.

FIELD OF THE INVENTION

The present invention relates to viability detection of bacterial spores and more particularly to real time detection of viable bacterial spores. This invention was made with government support under Contract No. W-7405-ENG-36 awarded by the U.S. Department of Energy. The government has certain rights in the invention.

BACKGROUND OF THE INVENTION

Some medically important bacteria such as *Bacillus anthracis, Bacillus cereus, Clostridium botulinum,* and *Clostridium perfringens* form endospores. Currently, detection of these and other bacterial spores are typically accomplished through antibody or DNA bases systems. One shortfall of these techniques is their inability to determine whether or not the detected spores are viable. As an example, naked DNA or spore coats (which do not constitute pathogenicity) may be erroneously perceived as infectious agents.

The need for rapid microbiological viability assays is well recognized in virtually all industries. Currently, culturing is the accepted method for viability detection, yet, viability testing for bacterial spores is typically a time consuming process that requires aseptic culture techniques and extended incubation periods upwards of 24 hours. Currently, there is no real time, positive viability detection available.

Recently, U.S. Pat. No. 5,795,730 described a rapid read-out biological indicator to assess or determine the effectiveness of a sterilization process including contacting an indicator containing microbial spores with a sterilant to give exposed spores, contacting the exposed spores with a medium selected to germinate the spores and calculating a rate of germination of the exposed spores to determine the effectiveness of the sterilization. The germination rate was determined using spectrophotometric or light scattering techniques related to measuring the light absorbance or scattering of ungerminated spores. The germination medium preferably included L-asparagine or L-glutamine.

Nevertheless, a need remains for a rapid, sensitive method for determining viability of bacteria spores in real time, e.g., for determining the effectiveness of sterilization procedures. Further, such a rapid, sensitive method would enhance the safety and protection of a civilian population from a terrorist-induced panic.

Some of the most potent biological agents are spore-forming bacteria. These bacterial can be produced and maintained in a dormant state and upon entering the human body, convert into their pathogenic form. The best known bacterial warfare agent is *Bacillus anthracis,* which causes the disease anthrax. This endospore-forming microbe can survive long periods of time in a dormant (spore) form. When these spores enter the lungs through airborne dispersal, they are converted from their dormant state to a vegetative state. In the vegetative state, these microbes produce toxins that enter cells and cause them to lyse. Cell lysis leads to extensive oedema of the tissues and is fatal.

The entire process by which dormant bacterial spores become vegetative cells is called germination. The length of time required to complete such a process has been documented as taking from a matter of minutes up to 40 minutes or more. Differences in bacterial strains can affect the duration of this process, but the reasons for these differences are unknown. However, early events in germination, generally referred to as initiation, can occur within minutes when the spores come in contact with the proper environment. Events in initiation of spore germination are commitment, in which some change in the spore begins an irreversible process not fully understood but including loss of heat resistance, release of cations, dipicolinic acid (DPA) and sulfolactic acid, and loss of spore cortex, refractivity and UV resistance. Initiation may only take 5 minutes for a spore population, so detection of these events can serve as an ideal target for a real time viability monitor.

Terbium chelation and other lanthanide chelation have been used to detect free DPA in solutions, and to detect chemical germination of *B. megaterium.* U.S. Pat. No. 5,876,960 by Rosen describes the use of this assay to detect the presence of bacterial spores, but there is no suggestion regarding the viability of the spores.

It is an object of this invention to provide a method for rapid viability detection of bacterial spores.

It is another object of this invention to provide a system for such a rapid viability detection of bacterial spores.

It is still another object of the present invention to provide a germination medium capable of promoting high germination levels of bacterial spores.

SUMMARY OF THE INVENTION

To achieve the foregoing and other objects, and in accordance with the purposes of the present invention, as embodied and broadly described herein, provides a process for detecting the presence of viable bacterial spores in a sample including placing a sample in a germination medium for a period of time sufficient for commitment of any present viable bacterial spores to occur, mixing said sample with a solution of a lanthanide capable of forming a fluorescent complex with dipicolinic acid, and, measuring said sample for the presence of dipicolinic acid.

The present invention further provides germination reaction mixture useful for promoting commitment of any viable bacterial spores including a combination of L-alanine, L-asparagine and D-glucose.

The present invention still further provides a system including a germination chamber having inlets from a sample chamber, a germinant chamber and a bleach chamber, said germination chamber further including an outlet through a filtering means, said outlet connected to a detection chamber, said detection chamber having an inlet from a fluorescence promoting metal chamber and said detection chamber including a spectral excitation source and a means of measuring emission spectra from a sample, said detection chamber further connected to a waste chamber.

BRIEF DESCRIPTION OF THE DRAWINGS

FIG. 1 shows a graph of a typical standard curve for DPA detection.

FIG. 2 shows a schematic drawing of a detection apparatus used with the present invention.

DETAILED DESCRIPTION

The present invention is concerned with a simple and rapid assay to detect viable bacterial spores. The present invention involves the combination of optimized germination and detection to provide for rapid viability detection.

A system and process for a rapid assay to detect viable bacterial spores has now been developed. The present invention employs an optimized spore germination solution, which is incubated with bacterial spores so the spores turn back into vegetative cells (germination). Dipicolinic acid (DPA) is a biomolecule unique to bacterial spores, neither present in vegetative cells, nor present in fungal cells or spores. This biomolecule is rapidly released during germination of viable bacterial endospores. When the filtered solution from the incubated spores is mixed with a solution of a lanthanide metal such as a solution of terbium nitrate, the terbium binds with the DPA and the resultant complex fluoresces 10,000-fold times more than the non-chelated materials. Free DPA is detected using fluorescence spectophotometry and concentrations can be converted to numbers of viable spores using a standard curve. Using the assay of the present invention, detection of as few as $5.8 \times 10^5$ viable bacterial spores can be achieved in less than 15 minutes, from start to finish.

Rather than comparing photoluminescence emission intensity of a sample with a threshold level, the quantification method could use a calibration curve from which the bacterial spore concentration can be determined from the emission intensity detected for the sample. Such a calibration curve can be determined in a quantification stage as follows. Two or more test samples are prepared using the same solution as used for a sample containing an unknown concentration of spores. A suitable lanthanide is combined with the test samples in the same molarity as used to prepare the sample with the unknown spore concentration. The test samples are subjected to photoluminescence testing by excitation and absorption or emission detection at the same wavelengths used for the sample with the unknown concentration of spores. The emission intensities determined for the test samples can be used to plot the calibration curve that functionally relates the emission intensity to known spore concentrations. Therefore, by interpolation or extrapolation between the emission intensities of the test samples of known spore concentrations, the emission intensity for a sample with unknown concentration can be used with the calibration curve to determine its spore concentration.

Other lanthanides can be used in place of the terbium. For example, solutions of europium and samarium can be used.

The present invention has been demonstrated with a proven laboratory technique using *Bacillus globigii* as a model spore forming bacterium. This unique approach can be employed as a stand alone detection system or added on to a variety of front end collection systems and used in conjunction with identification-type detection systems. The viability assay of the present invention may be employed to detect unwanted spore contamination in many different industrial sectors including aseptic processing, sterilization efficacy testing, and QA/QC testing. It may also be used in conjunction with more specific non-viability detection methods (i.e., antibody-based detection) to provide enhanced bacterial spore detection capabilities.

In this invention, a viability detection method was developed based on the germination process and demonstrated its rapidity and validity by testing it with a variety of endospore forming microbes. The selected model organism, *B. globigii*, and its optimized germinating conditions provided the basis of the rapid laboratory assay to detect viability in spores.

Endospore germination proceeds by the interaction of a germinant with the appropriate receptor and an irreversible commitment step. During the commitment step, a number of small molecules are released: glutamic acid, potassium, sodium, calcium, magnesium, and dipicolinic acid (pyridine-2,6-dicarboxylic acid, DPA). Of these, only DPA is unique to bacterial spores.

The release of DPA from spores in response to an optimized germinating solution was detected by DPA-terbium complexation. Terbium is a trivalent lanthanide that has been used extensively as a fluorescent probe in a range of biochemical studies. The terbium cation ($Tb^{3+}$) reacts with the dipicolinate anion ($DPA^{2-}$) to form the complex $[Tb(DPA)_3]^{3-}$, which is 10,000 times more fluorescent than terbium alone. This complex has a distinctive photoluminescence emission at 545 nm.

In one embodiment of the present inventions spores of a known concentration were mixed with an optimized germinant combination (equal molar L-alanine, L-asparagine and D-glucose) and allowed to incubate for 10 minutes. The solution was centrifuged and 500 $\mu$l of the supernatant was withdrawn and transferred to a different tube. 500 $\mu$l of 100 $\mu$M terbium nitrate was added and the sample was mixed and immediately analyzed. Photoluminescence emission spectra were measured from each sample with an Aminco-Simco Bowman series-2 luminescent spectrophotometer. Calibration curves were measured using DPA (25 $\mu$M to 120 $\mu$M) dissolved in sterile distilled water. Excitation was at 276 nm and the emission luminescence at 545 nm was measured for each datum point, which consisted of 3–9 replicates. Calibration measurements were repeated whenever the emission photomultiplier tube (PMT) voltage was changed. DPA content was normalized based on the following: $5.0 \times 10^8$ spores/ml=1 mg dry weight of spores.

In another embodiment of the present invention, the process was the same as described above with the following exception: Spores were filtered onto a polycarbonate membrane, exposed to germinant and the filter was then removed. The remaining liquid was used as the sample for mixing with terbium nitrate reagent.

In the present invention the complexation of terbium with DPA has allowed the detection of as few as 45 ng of DPA, which corresponds to approximately $5.0 \times 10^5 - 2.5 \times 10^6$ viable *B. globigii* spores. This process requires less than 10 minutes from initial sampling to detection. The benefits of this assay include a combination of time and ease. This assay is a significant improvement over traditional culturing techniques for viability and provides useful information beyond current DPA assays to detect formant spores.

The process of the present invention can serve as a viability detection method for aseptic manufacturing, as a viability detection method for hospitals and medical equipment, as a viability detection method for identifying a bioagent attack, and as a viability detection method for determination of the efficacy of a decontamination process. Additionally, the process of the present invention may serve as a viability detection method for the detection of viable spores in manufactured foods.

Figure 2:
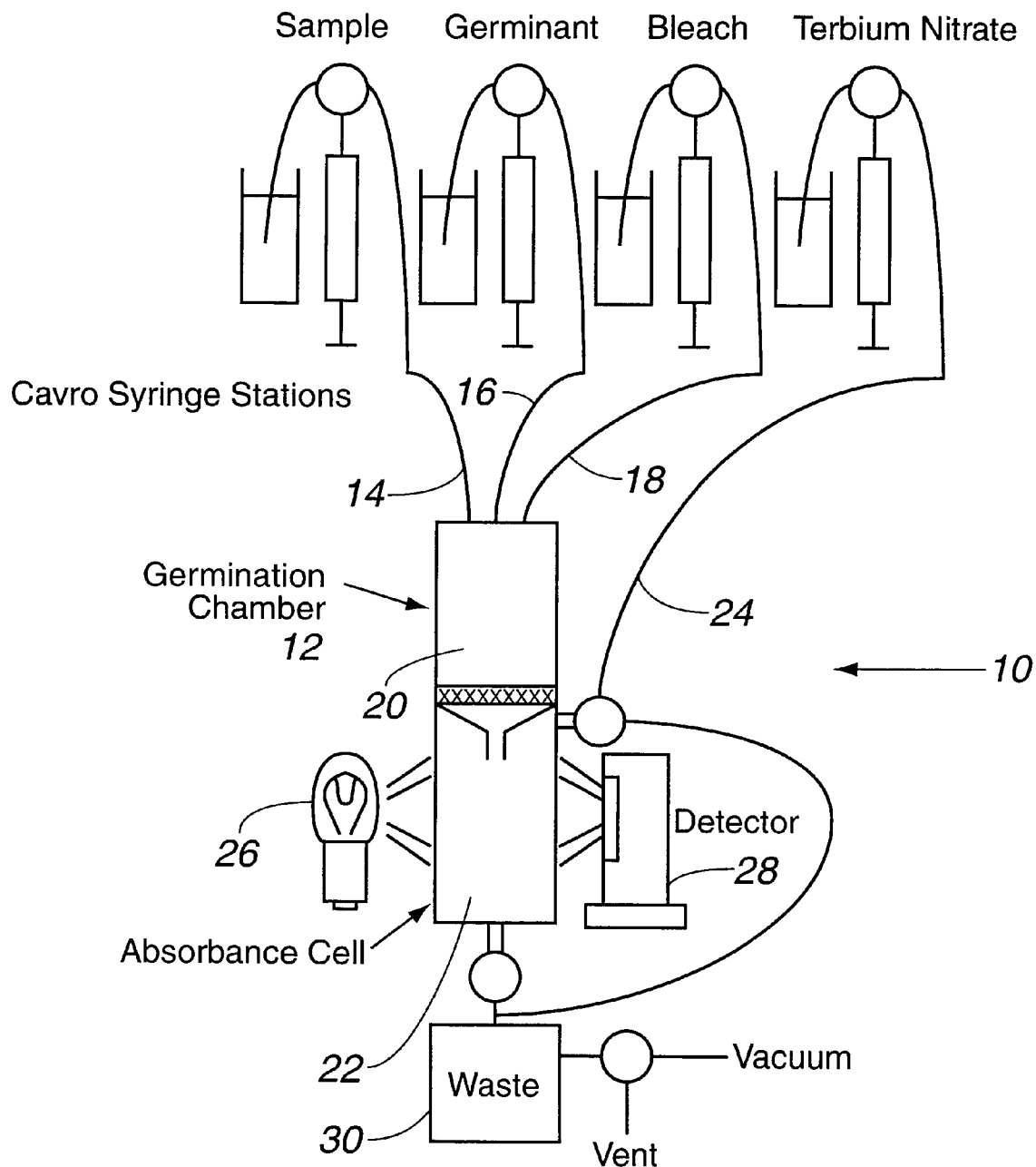

FIG. 2 shows a system 10 for practicing the process of the present invention. A germination chamber 12 includes inlets from a sample chamber 14, a germinant chamber 16 and a bleach chamber 18. A sample and a germinant would be entered into the germination chamber 12 whereupon a spore could undergo commitment. Bleach would be entered into the germination chamber only during a clean-up stage in-between sample determinations. After the spores have germinated, the sample is filtered through a filtering means 20 and the filtered sample passes into a detection chamber 22. Prior to the detection event, the filtered sample is mixed with a lanthanide such as terbium nitrate from a lanthanide metal chamber 24. Detection chamber 22 includes a light source 26 and a detector or detection means 28. Following the detection stage, the tested sample passes to waste chamber 30 which is attached to a vacuum line and a vent.

The present invention is more particularly described in the following examples, which are intended as illustrative only, since numerous modifications and variations will be apparent to those skilled in the art.

All biological media were supplied by Difco Laboratories (Detroit, Mich.). All chemical reagents were obtained from Aldrich Chemical Co. (Milwaukee, Wis.) and were of the highest purity available unless otherwise noted. *Bacillus subtilis* 1A1, *Bacillus megaterium* 7A16, *Bacillus cereus* 6A 1, *Bacillus thuringiensis* 4A1 and *Bacillus spaericus* 13A6 were obtained from the Bacillus Genetics Stock Center (Ohio State University, Columbus, Ohio). *Bacillus globigii* (*Bacillus subtilis* var. *niger*) was obtained from Life Sciences Division, Los Alamos National Laboratory, Los Alamos, N.Mex.). *Clostridium bifermentans* ATCC 638 was obtained from the American Type Culture Collection (Manassas, Va.). *Clostridium difficile* VPI 7698 was obtained from Department of Biochemistry, Virginia Tech, Blackburg, Va.).

All Bacillus species were grown in 2×Schaeffer's liquid sporulation medium or in Nutrient Broth (NB). Clostridium species were grown in PY broth in accordance with the procedure of Holderman et al., Anaerbode Laboratory Manual, $4^{th}$ ed., Virginia Polytechnic Institute and State University, Blackburg, Va.(1977).

EXAMPLE 1

Bacillus cultures were grown at 30° C. with moderate aeration for 7 days. Spores were harvested by centrifugation at 10,900×g for 30 minutes at 4° C. and resuspended in 200 milliliters (ml) of sterile distilled water and washed 7 to 10 times, heated to 65° C. for 15 minutes to kill any vegetative cells, and stored at 4° C. Spore populations were determined from the average of 3 serial dilution plates.

*B. globigii* spores (500 microliters ($\mu$l)) were diluted to a concentration of $3.6 \times 10^8$ spores per ml in 20 millimolar (mM) potassium phosphate buffer (pH 7.4), and mixed with 500 $\mu$l of a 0.12 M solution of one or more of L-alanine, L-asparagine and D-glucose, together with DPA and other chemicals to test the effectiveness of various combinations as germinating agents. The phase change of the spores in the germinants was monitored at 450 nm over a period of 10 minutes. The results of the various germinants are shown in Table 1.

TABLE 1

Relative germination based on the phase change of *Bacillus globigii* spores in different germinant mixtures

| Germinating mixture | Percent germination |
| --- | --- |
| 20 mM L-alanine, 20 mM L-asparagine and 20 mM D-glucose | 100.0 |
| 20 mM L-alanine and 20 mM D-glucose | 92.6 |
| 20 mM L-alanine and 20 mM L-asparagine | 90.7 |
| 20 mM L-alanine | 50.1 |
| 20 mM L-asparagine | 5.2 |
| 20 mM D-glucose | 7.0 |
| 20 mM DPA | 7.3 |

Surprisingly, the use of a mixture of L-alanine, L-asparagine and D-glucose was found to yield the highest germination percentages.

EXAMPLE 2

Spores (*B. globigii*) of a known concentration ($10^5$ spores/ml–$10^9$ spores/ml) were mixed with an optimized germinant combination (equal molar L-alanine, L-asparagine and D-glucose, 20 mM each) and allowed to incubate with shaking for 10 minutes. The solution was centrifuged at 14,000 rpm in an Eppendorf microcentrifuge and 500 $\mu$l of 100 micromolar ($\mu$M) terbium nitrate was added and the sample was mixed and immediately analyzed. Photoluminescence emission spectra were measured from each sample with an Aminco-Simco Bowman series-2 luminescent spectrophotometer (SLM-Aminco, Urban, Ill.). Calibration curves were measured using DPA (25 $\mu$M to 120 $\mu$M) dissolved in sterile distilled water. Excitation was at 276 nm and the emission luminescence at 545 nm was measured for each datum point, which consisted of 3–9 replicates. Calibration measurements were repeated whenever the emission photomultiplier tube (PMT) voltage was changed. DPA content was normalized based on the following: $5.0 \times 10^8$ spores/ml=1 mg dry weight of spores.

TABLE 2

Blind study comparison of methods for enumeration of viable *B. globigii* spores[a]

| Sample | Theoretical concentration (CFU/ml) | Experimental Concentration by DPA release (CFU/ml) | Experimental Concentration by dilution plating (CFU/ml) |
| --- | --- | --- | --- |
| 1* | $8.45 \times 10^8$ | $8.4 \times 10^8$ | $4.5 \times 10^8$ |
| 2* | $4.23 \times 10^7$ | $5.3 \times 10^8$ | $1.14 \times 10^7$ |
| 3+ | $1.07 \times 10^8$ | $8.1 \times 10^8$ | $5.70 \times 10^7$ |
| 4+ | $2.13 \times 10^8$ | $1.7 \times 10^8$ | $1.71 \times 10^8$ |

[a] A concentrated spore solution ($8.45 \times 10^8$) was diluted in sterile distilled water and the theoretical concentrations were recorded. DPA release and dilution plating were performed by individuals that were unaware of the theoretical concentrations of the spores in the diluted solutions.
*Spores generated in NB.
+Spores generated in Schaeffer's medium.

EXAMPLE 3

Same as example 2 with the following exception: Spores were filtered onto a polycarbonate membrane, exposed to the germinant and the filter was then removed. The remaining liquid was used as the sample for mixing with terbium nitrate reagent.

EXAMPLE 4

A known concentration ($10^5$ spores/ml–$10^9$ spores/ml) of other individual types of bacterial spores (*B. cereus, B. sphaericus, B. subtilis, B. anthacis* and *B. megaterium*) were treated in the manner of example 2. DPA from the viable bacterial spores of each type was detected by photoluminescence emission spectra as in example 2.

The results of the foregoing examples demonstrate that a germination medium including a combination of L-alanine, L-asparagine and D-glucose provides superior germination percentages of viable bacterial spores than any pair or individual amino acid from within combination. Further, the results of the foregoing examples demonstrate a rapid process of detecting the presence of viable bacterial spores in a sample.

Although the present invention has been described with reference to specific details, it is not intended that such details should be regarded as limitations upon the scope of the invention, except as and to the extent that they are included in the accompanying claims.

What is claimed is:

1. A process for detecting the presence of viable bacterial spores in a sample comprising:

placing a sample in a germination medium for a period of time sufficient for commitment of any present viable bacterial spores to occur;

mixing said sample with a solution of a lanthanide capable of forming a fluorescent complex with dipicolinic acid; and, measuring said sample for the presence of dipicolinic acid.

2. The process of claim 1 wherein said germination medium is a mixture of L-alanine, L-asparagine and D-glucose.

3. The process of claim 1 wherein said period of time is from about 10 minutes to about 1 hour.

4. The process of claim 1 wherein said lanthanide is terbium.

5. The process of claim 4 wherein said measuring of said sample is by fluorescense spectrophotometry.

6. A germination reaction mixture useful for promoting commitment of any viable bacterial spores in a sample comprising: a combination of L-alanine, L-asparagine as the only amino acids and, D-glucose.

7. The germination reaction mixture of claim 6 wherein said combination is in equimolar amounts of L-alanine, L-asparagine and D-glucose.

* * * * *